United States Patent [19]

Bell et al.

[11] Patent Number: 5,037,752

[45] Date of Patent: * Aug. 6, 1991

[54] MODIFIED TISSUE PLASMINOGEN ACTIVATOR SUBSTITUTED AT CYSTEINE-73 AND LYSINE-277

[75] Inventors: Leslie D. Bell, Chesterfield, Mo.; Ernest J. Mayer, King of Prussia, Pa.; Mark O. Palmier, Webster Groves, Mo.; H. Eser Tolunay, Creve Coeur, Mo.; Thomas G. Warren, Ballwin, Mo.; Tze-Chein Wun, St. Louis, Mo.

[73] Assignee: Monsanto Company, St. Louis, Mo.

[*] Notice: The portion of the term of this patent subsequent to Oct. 16, 2007 has been disclaimed.

[21] Appl. No.: 332,827

[22] Filed: Apr. 3, 1989

Related U.S. Application Data

[63] Continuation-in-part of Ser. No. 149,793, Jan. 29, 1988, Pat. No. 4,963,357, which is a continuation-in-part of Ser. No. 107,708, Oct. 9, 1987.

[51] Int. Cl.[5] .................. C12N 9/48; C12N 15/58; C12P 21/02; A61K 32/547
[52] U.S. Cl. .................. 435/226; 435/219; 435/320.1; 435/240.2; 536/27; 935/14; 935/70; 935/23; 935/27; 424/94.64
[58] Field of Search .............. 435/212, 320, 226, 219, 435/240.2, 69.6; 424/94.64; 935/14, 70; 536/27

[56] References Cited

U.S. PATENT DOCUMENTS

4,963,357  10/1990  Bell ........................... 424/94.64

FOREIGN PATENT DOCUMENTS

| | | |
|---|---|---|
| 178105 | 4/1986 | European Pat. Off. . |
| 227462 | 7/1987 | European Pat. Off. . |
| 234051 | 9/1987 | European Pat. Off. . |
| 242836 | 10/1987 | European Pat. Off. . |
| 86/01538 | 3/1986 | PCT Int'l Appl. . |
| 87/03906 | 7/1987 | PCT Int'l Appl. . |
| 2173804 | 10/1986 | United Kingdom . |

OTHER PUBLICATIONS

Pennica et al., Nature 301, 214–221 (1983).
Vehar, Bio/Technology 2(12), pp. 1051–1057 (1984).
Kagitani et al., FEBS Lett. 189(1), 145–149 (1985).
Zonneveld et al., Proc. Natl. Acad. Sci. USA 83, 4670–4674 (1986).
Verheijen et al., The EMBO J. 5(13), 3525–3530 (1986).
Ehrlich et al., Fibrinolysis 1, 75–81 (1987).
Klausner, Bio/Technology 4, 706–710 (1986).
Klausner, Bio/Technology 5, 869–870 (1987).
Lau et al., Bio/Technology 5(9), 953–958 (1987).

*Primary Examiner*—Richard A. Schwartz
*Assistant Examiner*—Marianne Porta
*Attorney, Agent, or Firm*—Scott J. Meyer; James W. Williams, Jr.

[57] ABSTRACT

A modified tissue plasminogen activator having an improved in vivo half-life characterized in that the normal protein moiety of 527 amino acids is mutated at the site Cys73→Arg and at the site Lys277→Asp.

12 Claims, 19 Drawing Sheets

```
<Cla I       >< Nde I                                                           >< 
CGATAAGCTATGTCTTACCAAGTCATATGTAGAGACGAAAAGACTCAAATGATCTACCAACAACACCAATCTTGGTTGAG
TATTCGATACAGAATGGTTCAGTATACATCTCTGCTTTCTGAGTTTACTAGATGGTTGTTGTGGTTAGAACCAACTC         80
                                                        ><

ACCAGTTTGCGTTCTAACAGAGTCGAATACTGTTGGTGTAACAGGGCCGCGCTCAATGTCACTCTGTTCCAGTCAAGT
TGGTCAAAACGCAAGATTGTCTCAGCTTATGACAACCACATTGTCGCGGCGCGAGTTACAGTGAGACAAGGTCAGTTCA    160
                        ><                                              ><

CTTGTTCCGAACCAAGATGTTTCAACGGTGGTACTTGCCAACAGGCCTTGTATTTCTGACTTCGTCTGTCAATGTCCA
GAACAAGGCTTGGTTCTACAAAGTTGCCACCATGAACGGTTGTCCGGAACATAAAGAGACTGAAGCAGACAGTTACAGGT    240
           ><                                          ><
         >  Mlu I      <

GAAGGTTCGCTGGTAAGTGTTGTGAAATCGACACGGTGCTACTTGTTACGAAGACCAAGGTATTAGCTACAGAGGTAC
CTTCCAAGCGACCATTCACAACACTTTAGCTGTGCGCACGATGAACAATGCTTCTGGTTCCATAATCGATGTCTCCATG    320
                                                           ><
><                    >      <

CTGGTCTACCGGCGGAATCTGGGCGGCCGAATGTACCAACTGGAACTCTTCCGCTTTGGCCCAAAAGCCATACTCTGGTCGAC
GACCAGATGGCCGCCTTAGACCCGCCGGCTTACATGGTTGACCTTGAGAAGGCGAAACCGGGTTTTCGGTATGAGACCAGCTG    400
                                                              ><

GCCCAGACGCCATCAGATTGGGTAATCACAACTACTGTAGAAAACCCGATCGTGATTCTAAGCCTTGGTGTTAC
CGGGTCTGCGGTAGTCTAACCCAAACCATTAGTGTTGATGACATCTTTGGGGCTAGCACTAAGATTCGGAACCACAATG    480
                                                            ><
><     ><EcoR I

GTTTCAAGGCTGGTAAATACTCTTCGAATTCTGTCTACTCCAGCATGCTCTGAAGGTAACTCTGACTGTTACTTCGG
CAAAAGTTCCGACCATTTATGAGAAGCTTAAGACAAGATGAGGTCGTACGAGACTTCCATTGAGACTGACAATGAAGCC    560
   ><                                                     ><
```

FIG.IA

```
                                                                            X
TAACGGTTCTGCTTACAGAGGTACCCACTCGTTAACTGAATCTGGTGCTTCCTGTTGCCATGGAACTCTATGATCTTGA  640
ATTGCCAAGACGAATGTCTCCATGGGTGAGCAATTGACTTAGACCAAACGTACCTTGAGATACTAGAACT
     X                              X              Nco I           X

TTGGTAAGGTCTACACCGCTCAAAACCCATCTGCTCAAGCCTTGGGTAGACGAGTTCGGAACCAAACCCAAACTACTGTAGAAACCCAGAC  720
AACCATTCCAGATGTGGCGAGTTTTGGGTAGACGAGTTCGGAACCCAAACCCATTCGTGTTGATGACATCTTTGGGTCTG
                    X                             X                   X

GGTGACGCTAAGCCTTGGTGTCACGTTTGAAGAACAGAGTCTTACTTGGGAGTACTGTGACGTTCCCAGCTGTTCTAC  800
CCACTGCGATTCGGAACCACAGTGCAAAACTCTGTCTCAGAATGAACCCTCATGACACTGCAAGGTCGACAAGATG
           X                X                                          X

CTGTGGTTTGAGACAATACTCTCAACCACAATTCAGAATTAAAGGTTGGTTTATTCGCTGACATCGCGAGCCATCCTTGGC  880
GACACCAAACTCTGTTATGAGAGTTGGTGTTAAGTCTTAATTTCCACCAAATAAGCGACTGTAGCGCTCGGTAGGAACCG
                               Bgl II<                X

AAGCTGCCATCTTCGCCAAGCACAGAAGATCTCCAGGTGAAAGATTCTTGTGTGGTATTTGATCAGCTCTTGTTGG  960
TTCGACGGTAGAGAAGCGGGTTCGTGTCTTCTAGAGGTCCACTGTTCTAAGAACACACCATAAACTAGTCGAGAACAACC
                                                           X

ATTTTGTCTGCTGCCACTGTTTCCAAGAAAGATTCCACCTCACCATTTGACTGTTATCTTGGGTAGAACCTACAGAGT  1040
TAAAACAGACGACGGGTGACAAAGGTTCTTTCTAAGGTGGAGTGGTAAACTGACAATAGAACCCATCTTGGATGTCTCA
                     X                   X                               X

CGTTCCCGGGGAAGAGGAACAAAGTTCGAAGTTGAAAAGTACATCGTTCACAAGGAATTTGACGATGACACTTACGACA  1120
GCAAGGGCCCCTTCTCCTTGTTTCAAGCTTCAACTTTTTCATGTAGCAAGTGTTCCTTAAACTGCTACTGTGAATGCTGT
 Av q I     X                                                        X

FIG. 1B
```

```
                                                                           X
                                                                          1200
ACGATATCGCTTTGTTACAATTGAAGTCTGACTCTTCCAGATGGCGGCAAGAATCTTCCGTCGTTAGAACCGTCTGTTG
TGCTATAGCGAAACAATGTTAACTTCAGACTGAGAAGGTCTACGCGGCGTTCTTAGAAGGCAGCAATCTTGGCAGACAAAC
                       X                                  X
                     Sac I                                               1280
CCACCGGGCCGACTTGCAATTGCCAGACTGGACTGAATGTGAGCTCTCTGGTTACGGTAAGCACGAAGCCTTGTCTCCATT
GGTGGCCGGCTGAACGTTAACGGTCTGACCTGACTTACACTCGAGAGACCAATGCCATTCGTGCTTCGGAACAGAGGTAA
                                   X       X
                                    XXba I                               1360
CTACTCTGAAAGATTGAAGGAAGCTCACGTTAGATTGTACCCATCTTCTAGATGTACCTCTCAACACTTGTTGAACAGAA
GATGAGACTTTCTAACTTCCTTCGAGTGCAATCTAACATGGGTAGAAGATCTACATGGAGAGTTGTGAACAACTTGTCTT
                                                     X                  1440
CTGTTACCGACAACATGTGTGTGCTGGTGACACCCGTTCTGGTGGGCCCAAGCTAACTTGCACGACGCTTGTCAAGGT
GACAATGGCGTTGTTGTACAACACGACCACTGTGGGCAAGACCACCCGGGGTTCGATTGAACGTGCTGCGAACAGTTCCA
                        X                             X
                                                                        1520
GACTCTGGTGGTCCATTGGTCTGTTTGAACGACGGTCGAATGACCTTGGTTATCATTCTTCTTGGGGTTTGGGTTGTGG
CTGAGACCACCAGGTAACCAGACAAACTTGCTGCCAGCTTACTGGAACCATAGTAAAGAAGAACCCAAACCCAAACACC
                                                                    X
                                                                   Hind 1600
CCAAAAGGACGTTCCAGGTGTTACACCAAGGTCACCAACTACTAGACTGGATCAGAGAGACAACATGAGACCATAATAAA
GGTTTTCCTGCAAGGTCCACAAATGTGGTTCCAGTGGTTGATGAATCTGACCTAGTCTCTGTTGTACTCTGGTATTATTT
                                                                       X
III BamH I   1609
GCTTG
CGAACCTAG
```

FIG. 1C

```
              M  D  A  M  K  R  G  L  C  C  V  L  L  L  C  G  A
CGATAAGCTTGCAATCATGGATGCAATGAAGAGAGGGCTCTGCTGTGTGCTGTGTGTGGAGCA
TATTCGAACGTTAGTACCTACGTTACTTCTCTCCCGAGACGACACGACGACGACACCTCGT

V  F  V  S  P  S  Q  E  I  H  A  R  F  R  R  G  A  R—S  Y  Q  V  I
GTCTTCGTTTCGCCCAGCCAGGAAATCCATGCCCGATTCAGAAGAGGAGCCAGATCTTACCAAGTCA
CAGAAGCAAAGCGGGTCGGTCCTTTAGGTACGGGCTAAGTCTTCTCCTCGGTCTAGAATGGTTCAGTAT
```

```
1
GGATCCGGCGATAAGCTTGCAATC  ATG GAT GCA ATG AAG AGA GGG CTC TGC TGT GTG CTG       60
                          Met Asp Ala Met Lys Arg Gly Leu Cys Cys Val Leu
                          -35                          -30

CTG TGT GGA GCA GTC TTC GTT  TCG CCC AGC CAG GAA ATC CAT GCC CGA TTC AGA AGA    120
Leu Cys Gly Ala Val Phe Val  Ser Pro Ser Gln Glu Ile His Ala Arg Phe Arg Arg
                -20                                  -10

GGA GCC AGA TCT TAC CAA ATA TGT  AGA GAC GAA AAG ACT CAA CAA ATG TAC CAA CAA    180
Gly Ala Arg Ser Tyr Gln Ile Cys  Arg Asp Glu Lys Thr Gln Gln Met Tyr Gln Gln
           1                                    10

CAC CAA TCT TGG TTG AGA CCA GTT  TCT AAC AGA GTC AAG TAC TGT GAA TAC TGG TGT CAA    240
His Gln Ser Trp Leu Arg Pro Val  Ser Asn Arg Val Lys Tyr Cys Glu Tyr Cys Trp Asn
          20                                   30

AGC GGC CGC GCT CAA TGT CAC TCT GTT CCA GTC AAG TCT TGT TCC GAA CCA AGA TGT TTC   300
Ser Gly Arg Ala Gln Cys His Ser Val Pro Val Lys Ser Cys Ser Glu Pro Arg Cys Phe
        40                                   50

AAC GGT GGT ACT TGC CAA CAG GCC TTG TAT TTC TCT GAC TTC GTC CGT CAA TGT CCA GAA   360
Asn Gly Gly Thr Cys Gln Gln Ala Leu Tyr Phe Ser Asp Phe Val Arg Gln Cys Pro Glu
         60                                   70    73

GGT TTC GCT GGT AAG TGT TGT GAA ATC GAC ACG CGT GCT ACT TGT TAC GAA GAC CAA GGT   420
Gly Phe Ala Gly Lys Cys Cys Glu Ile Asp Thr Arg Ala Thr Cys Tyr Glu Asp Gln Gly
        80                                   90
```

FIG. 5A(ii)

```
ATT AGC TAC AGA GGT ACC TGG TCT ACC GCG GAA TCT ACC TGT GAA TGG AAC    480
Ile Ser Tyr Arg Gly Thr Trp Ser Thr Ala Glu Ser Thr Cys Glu Trp Asn
             100                                        110

TCT TCC GCT TTG GCC CAA AAG CCA TAC TCT GGT CGA CGC CCA GAC GCC ATC AGA TTG GGT    540
Ser Ser Ala Leu Ala Gln Lys Pro Tyr Ser Gly Arg Arg Pro Asp Ala Ile Arg Leu Gly
             120                                        130

TTG GGT AAT CAC AAC TAC TGT AGA AAC CCC GAT CGT GAT TCT AAG CCT TGG TGT TAC GTT    600
Leu Gly Asn His Asn Tyr Cys Arg Asn Pro Asp Arg Asp Ser Lys Pro Trp Cys Tyr Val
             140                                        150

TTC AAG GCT GGT AAA TAC TTC TCC GAA TTC TGT TCT ACT CCA GCA TGC TCT GAA GGT AAC    660
Phe Lys Ala Gly Lys Tyr Phe Ser Glu Phe Cys Ser Thr Pro Ala Cys Ser Glu Gly Asn
             160                                        170

TCT GAC TGT TAC TTC GGT AAC GGT TCT GCT TAC AGA GGT ACC CAC TCG TTA ACT GAA TCT    720
Ser Asp Cys Tyr Phe Gly Asn Gly Ser Ala Tyr Arg Gly Thr His Ser Leu Thr Glu Ser
             180                                        190

GGT GCT TCC TGT TTG CCA TGG AAC TCT ATG ATC TTG ATT GGT AAG GTC TAC ACC GCT CAA    780
Gly Ala Ser Cys Leu Pro Trp Asn Ser Met Ile Leu Ile Gly Lys Val Tyr Thr Ala Gln
             200                                        210
```

```
AAC CCA TCT GCT CAA GCC TTG GGT TTG AAG CAC AAC TAC TGT AGA AAC CCA GAC GGT
Asn Pro Ser Ala Gln Ala Leu Gly Leu Lys His Asn Tyr Cys Arg Asn Pro Asp Gly
                                            230                           840

GAC GCT AAG CCT TGG TGT CAC GTT TTG AAG AAC AGA CGT CTT ACT TGG GAG TAC TGT GAC
Asp Ala Lys Pro Trp Cys His Val Leu Lys Asn Arg Arg Leu Thr Trp Glu Tyr Cys Asp
        240                                     250                           900

GTT CCC AGC TGT TCT ACC TGT GGT GGT TTG AGA CAA TAC TGT CAA CCA CAA TTC AGA ATT AAA
Val Pro Ser Cys Ser Thr Cys Gly Gly Leu Arg Gln Tyr Cys Gln Pro Gln Phe Arg Ile Lys
        260                                     270                                   960

GGT TTA TTC GCT GAC ATC GCG AGC CAT CCT TGG CAA GCT GCC ATC TTC GCC AAG CAC
Gly Leu Phe Ala Asp Ile Ala Ser His Pro Trp Gln Ala Ala Ile Phe Ala Lys His
        280                                     290                           1020

AGA AGA TCT CCA GGT GAA AGA TTC TTG TGT GGT GGT GGG ATT TTG ATC AGC TCT TGT TGG ATT
Arg Arg Ser Pro Gly Glu Arg Phe Leu Cys Gly Gly Gly Ile Leu Ile Ser Ser Cys Trp Ile
        300                                     310                                   1080

TTG TCT GCT GCC CAC TGT TTC CAA GAA AGA TTC CCA CAC CAT TTG ACT GTT ATC TTG
Leu Ser Ala Ala His Cys Phe Gln Glu Arg Phe Pro His His Leu Thr Val Ile Leu
        320                                     330                           1140
```

FIG. 5B(i)

| | | | | | | | | | 1200 |
|---|---|---|---|---|---|---|---|---|---|
| GGT | AGA | ACC | TAC | AGA | GTC | GTT | CCC | GGG | GAA | GAG | GAA | CAA | AAG | TTC | GAA | GTT | GAA | AAG | TAC |
| Gly | Arg | Thr | Tyr | Arg | Val | Val | Pro | Gly | Glu | Glu | Glu | Gln | Lys | Phe | Glu | Val | Glu | Lys | Tyr |
| | | 340 | | | | | | | | | 350 | | | | | | | | |

| | | | | | | | | | 1260 |
|---|---|---|---|---|---|---|---|---|---|
| ATC | GTT | CAC | AAG | GAA | TTT | GAC | GAT | GAC | ACT | TAC | GAC | AAC | GAT | ATC | GCT | TTG | TTA | CAA | TTG |
| Ile | Val | His | Lys | Glu | Phe | Asp | Asp | Asp | Thr | Tyr | Asp | Asn | Asp | Ile | Ala | Leu | Leu | Gln | Leu |
| | | 360 | | | | | | | | | 370 | | | | | | | | |

| | | | | | | | | | 1320 |
|---|---|---|---|---|---|---|---|---|---|
| AAG | TCT | GAC | TCT | TCC | AGA | TGC | GCG | CAA | TCT | TCC | GTC | GTT | AGA | ACC | GTC | TGT | TTG | CCA |
| Lys | Ser | Asp | Ser | Ser | Arg | Cys | Ala | Gln | Ser | Ser | Val | Val | Arg | Thr | Val | Cys | Leu | Pro |
| | | 380 | | | | | | | | | 390 | | | | | | | | |

| | | | | | | | | | 1380 |
|---|---|---|---|---|---|---|---|---|---|
| CCG | GCC | TTG | CAA | TTG | CCA | GAC | TGG | ACT | GAA | TGT | GAG | CTC | TCT | GGT | TAC | GGT | AAG | CAC |
| Pro | Ala | Leu | Gln | Leu | Pro | Asp | Trp | Thr | Glu | Cys | Glu | Leu | Ser | Gly | Tyr | Gly | Lys | His |
| | | 400 | | | | | | | | | 410 | | | | | | | | |

| | | | | | | | | | 1440 |
|---|---|---|---|---|---|---|---|---|---|
| GAA | GCC | TTG | TCT | CCA | TTC | TAC | TCT | GAA | AGA | TTG | AAG | GAA | GCT | CAC | GTT | AGA | TTG | TAC | CCA |
| Glu | Ala | Leu | Ser | Pro | Phe | Tyr | Ser | Glu | Arg | Leu | Lys | Glu | Ala | His | Val | Arg | Leu | Tyr | Pro |
| | | 420 | | | | | | | | | 430 | | | | | | | | |

| | | | | | | | | | 1500 |
|---|---|---|---|---|---|---|---|---|---|
| TCT | TCT | AGA | TGT | ACC | TCT | CAA | CAC | TTG | AAC | TTG | TTG | AAC | AGA | ACT | GTT | ACC | GAC | AAC | ATG | TTG | TGT |
| Ser | Ser | Arg | Cys | Thr | Ser | Gln | His | Leu | Asn | Leu | Leu | Asn | Arg | Thr | Val | Thr | Asp | Asn | Met | Leu | Cys |
| | | 440 | | | | | | | | | 450 | | | | | | | | |

| | | | | | | | | | 1560 |
|---|---|---|---|---|---|---|---|---|---|
| GCT | GGT | GAC | ACC | CGT | TCT | GGT | GGG | CCC | CAA | GCT | AAC | TTG | CAC | GAC | GCT | TGT | CAA | GGT | GAC |
| Ala | Gly | Asp | Thr | Arg | Ser | Gly | Gly | Pro | Gln | Ala | Asn | Leu | His | Asp | Ala | Cys | Gln | Gly | Asp |
| | | 460 | | | | | | | | | 470 | | | | | | | | |

FIG. 5B(ii)

```
TCT GGT CCA TTG GTC TGT TTG AAC GAC GGT CGA ATG ACC TTG GTT GGT ATC ATT TCT
Ser Gly Pro Leu Val Cys Leu Asn Asp Gly Arg Met Thr Leu Val Gly Ile Ile Ser
        480                             490                           1620

TGG GGT TGT GGC CAA AAG GAC GTT CCA GGT TAC ACC AAG GTC ACC AAC TAC
Trp Gly Cys Gly Gln Lys Asp Val Pro Gly Tyr Thr Lys Val Thr Asn Tyr
        500                             510                   1680

TTA GAC TGG ATC AGA GAC AAC ATG AGA CCA TAA TAA AGC TT
Leu Asp Trp Ile Arg Asp Asn Met Arg Pro End End
        520                             527      1721
```

FIG. 5C

```
1
GGATCCGGCGATAAGCTTGCAATC ATG GAT GCA ATG AAG AGA GGG CTC TGC TGT GTG CTG     60
                         Met Asp Ala Met Lys Arg Gly Leu Cys Cys Val Leu
                         -35                     -30

CTG TGT GGA GCA GTC TTC GTT TCG CCC AGC CAG GAA ATC CAT GCC CGA TTC AGA AGA   120
Leu Cys Gly Ala Val Phe Val Ser Pro Ser Gln Glu Ile His Ala Arg Phe Arg Arg
         -20                                         -10

GGA GCC AGA TCT TAC CAA GTC ATA TGT AGA GAC GAA AAG ACT CAA ATG ATC TAC CAA   180
Gly Ala Arg Ser Tyr Gln Val Ile Cys Arg Asp Glu Lys Thr Gln Met Ile Tyr Gln
         1                               10

CAA CAC CAA TCT TGG TTG AGA CCA GTT TTG CGT TCT AAC AGA GTC GAA TAC TGT TGG   240
Gln His Gln Ser Trp Leu Arg Pro Val Leu Arg Ser Asn Arg Val Glu Tyr Cys Trp
             20                              30

TGT AAC AGC GGC CGC GCT CAA TGT CAC TCT GTT CCA GTC AAG TCT TGT TCC GAA CCA   300
Cys Asn Ser Gly Arg Ala Gln Cys His Ser Val Pro Val Lys Ser Cys Ser Glu Pro
             40                              50

AGA TGT TTC AAC GGT GGT ACT TGC CAA CAG GCC TTG TAT TTC TCT GAC TTC GTC TGT   360
Arg Cys Phe Asn Gly Gly Thr Cys Gln Gln Ala Leu Tyr Phe Ser Asp Phe Val Cys
                 60                              70

CAA TGT CCA GAA GGT TTC GCT GGT AAG TGT TGT GAA ATC GAC ACG CGT GCT ACT TGT   420
Gln Cys Pro Glu Gly Phe Ala Gly Lys Cys Cys Glu Ile Asp Thr Arg Ala Thr Cys
                     80                              90

GAA GAC CAA GGT
Tyr Glu Asp Gln Gly
```

FIG. 9A(i)

```
ATT AGC TAC AGA GGT ACC TGG TCT ACC GCG GAA TCT GGC GCC GAA TGT ACC AAC TGG AAC   480
Ile Ser Tyr Arg Gly Thr Trp Ser Thr Ala Glu Ser Gly Ala Glu Cys Thr Asn Trp Asn
        100                             110

TCT TCC GCT TTG GCC CAA AAG CCA TAC TCT GGT CGA CGC CCA GAC GCC ATC AGA TTG GGT   540
Ser Ser Ala Leu Ala Gln Lys Pro Tyr Ser Gly Arg Arg Pro Asp Ala Ile Arg Leu Gly
        120                             130

TTG GGT AAT CAC AAC TAC TGT AGA AAC CCC GAT CGT GAT TCT AAG CCT TGG TGT TAC GTT   600
Leu Gly Asn His Asn Tyr Cys Arg Asn Pro Asp Arg Asp Ser Lys Pro Trp Cys Tyr Val
        140                             150

TTC AAG GCT GGT AAA TAC TCT TCC GAA TTC TGT TCT ACT CCA GCA TGC TCT GAA GGT AAC   660
Phe Lys Ala Gly Lys Tyr Ser Ser Glu Phe Cys Ser Thr Pro Ala Cys Ser Glu Gly Asn
        160                             170

TCT GAC TGT TAC TTC GGT AAC GGT TCT GCT TAC AGA GGT ACC CAC TCG TTA ACT GAA TCT   720
Ser Asp Cys Tyr Phe Gly Asn Gly Ser Ala Tyr Arg Gly Thr His Ser Leu Thr Glu Ser
        180                             190

GGT GCT TCC TGT TTG CCA TGG AAC TCT ATG ATC TTG ATT GGT AAG GTC TAC ACC GCT CAA   780
Gly Ala Ser Cys Leu Pro Trp Asn Ser Met Ile Leu Ile Gly Lys Val Tyr Thr Ala Gln
        200                             210
```

FIG. 9A(ii)

```
AAC CCA TCT GCT CAA GCC TTG GGT AAG CAC AAC TAC TGT AGA AAC CCA GAC GGT
Asn Pro Ser Ala Gln Ala Leu Gly Lys His Asn Tyr Cys Arg Asn Pro Asp Gly
        220                             230                           840

GAC GCT AAG CCT TGG TGT CAC GTT TTG AAG AAC AGA CGT CTT ACT TGG GAG TAC GAC
Asp Ala Lys Pro Trp Cys His Val Leu Lys Asn Arg Arg Leu Thr Trp Glu Tyr Asp
        240                             250                           900

GTT CCC AGC TGT TCT ACC TGT GGT TTG AGA CAA TAC TCT CAA CCA CAA TTC AGA ATT GAC
Val Pro Ser Cys Ser Thr Cys Gly Leu Arg Gln Tyr Ser Gln Pro Gln Phe Arg Ile Asp
        260                             270                           960    277

GGT GGT TTA TTC GCT GAC ATC GCG AGC CAT CCT TGG CAA GCT GCC ATC TTC GCC AAG CAC
Gly Gly Leu Phe Ala Asp Ile Ala Ser His Pro Trp Gln Ala Ala Ile Phe Ala Lys His
        280                             290                          1020

AGA AGA TCT CCA GGT GAA AGA TTC TTG TGT GGT GGT ATT TTG ATC AGC TCT TGT TGG ATT
Arg Arg Ser Pro Gly Glu Arg Phe Leu Cys Gly Gly Ile Leu Ile Ser Ser Cys Trp Ile
        300                             310                          1080

TTG TCT GCT GCC CAC TGT TTC CAA GAA AGA TTC CCA CCT CAC CAT TTG ACT GTT ATC TTG
Leu Ser Ala Ala His Cys Phe Gln Glu Arg Phe Pro Pro His His Leu Thr Val Ile Leu
        320                             330                          1140
```

FIG. 9B(i)

```
GGT AGA ACC TAC AGA GTC GTT CCC GGG GAA GAG GAA CAA AAG TTC GAA GTT GAA AAG TAC   1200
Gly Arg Thr Tyr Arg Val Val Pro Gly Glu Glu Glu Gln Lys Phe Glu Val Glu Lys Tyr
        340

ATC GTT CAC AAG GAA TTT GAC GAT GAC ACT TAC GAC AAC GAT ATC GCT TTG TTA CAA TTG   1260
Ile Val His Lys Glu Phe Asp Asp Asp Thr Tyr Asp Asn Asp Ile Ala Leu Leu Gln Leu
        360                                     370

AAG TCT GAC TCT TCC AGA TGC GCG CAA GAA TCT GTC GTT AGA ACC GTC TGT TTG CCA       1320
Lys Ser Asp Ser Ser Arg Cys Ala Gln Glu Ser Val Val Arg Thr Val Cys Leu Pro
        380                                     390

CCG GCC GAC TTG CAA TTG CCA GAC TGG ACT GAA TGT CTC TCT GGT TAC GGT AAG CAC       1380
Pro Ala Asp Leu Gln Leu Pro Asp Trp Thr Glu Cys Leu Ser Gly Tyr Gly Lys His
        400                                     410

GAA GCC TTG TCT CCA TTC TAC TCT GAA AGA TTG AAG GAA GCT CAC GTT AGA TTG TAC CCA   1440
Glu Ala Leu Ser Pro Phe Tyr Ser Glu Arg Leu Lys Glu Ala His Val Arg Leu Tyr Pro
        420                                     430

TCT TCT AGA TGT ACC TCT CAA CAC TTG AAC AGA ACT GTT ACC GAC AAC ATG TTG TGT       1500
Ser Ser Arg Cys Thr Ser Gln His Leu Asn Arg Thr Val Thr Asp Asn Met Leu Cys
        440                                     450

GCT GGT GAC ACC CGT TCT GGT GGG CCC CAA GCT AAC TTG CAC GCT TGT CAA GGT GAC       1560
Ala Gly Asp Thr Arg Ser Gly Gly Pro Gln Ala Asn Leu His Ala Cys Gln Gly Asp
        460                                     470
```

FIG. 9B(ii)

```
TCT GGT GGT CCA TTG GTC TGT TTG AAC GAC GGT CGA ATG ACC TTG GTT GGT ATC ATT TCT
Ser Gly Gly Pro Leu Val Cys Leu Asn Asp Gly Arg Met Thr Leu Val Gly Ile Ile Ser
        480                                     490                         1620

TGG GGT TGT GGC CAA AAG GAC GTT CCA GGT GTT TAC ACC AAG GTC ACC AAC TAC
Trp Gly Cys Gly Gln Lys Asp Val Pro Gly Val Tyr Thr Lys Val Thr Asn Tyr
        500                                     510                 1680

TTA GAC TGG ATC AGA GAC AAC ATG AGA CCA TAA TAA AGC TT
Leu Asp Trp Ile Arg Asp Asn Met Arg Pro End End
        520                             527      1721
```

ProGlnPheArgIleLysGlyGlyLeuPhe
ccacaattcagaattaaaggtggtttattc
5' aattcagaattgacggtggttta 3'
ccacaattcagaattgacggtggtttattc
ProGlnPheArgIleAspGlyGlyLeuPhe

MODIFIED TISSUE PLASMINOGEN ACTIVATOR SUBSTITUTED AT CYSTEINE-73 AND LYSINE-277

CROSS-REFERENCE TO RELATED APPLICATIONS

This is a continuation-in-part of copending application Ser. No. 07/149,793, filed Jan. 29, 1988, now U.S. Pat. No. 4,963,357, which in turn is a continuation-in-part of application Ser. No. 07/107,708, filed Oct. 9, 1987.

BACKGROUND OF THE INVENTION

This invention relates to plasminogen activators which are useful thrombolytic agents. More particularly, this invention relates to a modified tissue plasminogen activator having an improved in vivo half-life.

It is known that various plasminogen activators (PA) are widely distributed throughout the body and can be purified from tissue extracts. Typical examples of tissue sources are kidney, lung and uterus tissues. The best characterized of these plasminogen activators fall into two major groups, urokinase plasminogen activator (u-PA) and tissue plasminogen activator (t-PA). u-PA and t-PA are present in ng/ml concentrations in human plasma but are immunologically unrelated. t-PA has been demonstrated to have higher affinity for fibrin than u-PA. u-PA products isolated and purified from human urine and from mammalian kidney cells are pharmaceutically available as thrombolytic agents.

Due to the extremely low concentration of t-PA in blood and tissue extracts, other sources and means of producing this preferred thrombolytic agent have been sought after.

One method of producing t-PA on a large scale comprises isolating the protein from the culture fluid of human melanoma cells grown under in vitro cell culture conditions. An established human melanoma cell line (Bowes) has been used for this purpose. See, for example, European Patent Application 41,766, published Dec. 16, 1981; Rijken and Collen, *J. Biol. Chem.* 256(13), 7035–7041 (1981); and Kluft et al., *Adv. Biotech. Proc.* 2, Alan R. Liss, Inc., 1983, pp. 97–110. The Bowes melanoma t-PA is a glycoprotein which has a molecular weight of about 68,000–70,000 daltons and a 527 amino acid structure with serine at the $NH_2$-terminus. The melanoma t-PA can exist as two chains, an A-chain and a B-chain. It also separates into two variants (or isoforms) in the A-chain, known as types I and II, which differ by about $M_r$ 2000–3000. See Ranby et al., *FEBS Lett.* 146 (2), 289–292 (1982), and Wallen et al., *Eur. J. Biochem.* 132, 681–686 (1983). Type I is glycosylated at Asn-117, Asn-184 and Asn-448 whereas Type II is glycosylated only at Asn-117 and Asn-448 according to Pohl et al., *Biochemistry* 23, 3701–3707 (1984). A high mannose structure has been assigned to Asn-117 whereas two complex carbohydrate structures are assigned to Asn-184 and Asn-448 by Pohl et al., "EMBO Workshop on Plasminogen Activators," Amalfi, Italy, Oct. 14–18, 1985.

Genetic information from the Bowes melanoma cell line also has been embodied in *E. coli* by conventional recombinant DNA gene splicing methods to permit the production of the t-PA protein moiety by that microorganism. See, for example, UK Patent Application 2,119,804, published Nov. 23, 1983; Pennica et al., *Nature* 301, 214–221 (1983); and Vehar et al., *Bio/Technology* 2 (12), 1051–1057 (1984). Recombinant t-PA produced by the expression of Bowes melanoma genetic material in cultured mammalian cells has been administered to humans with some measure of effectiveness. See Collen et al., *Circulation* 70(16), 1012–1017 (1984).

The recombinant-derived t-PA produced in *E. coli* is non-glycosylated and contains only the protein moiety of t-PA. Although the specific function of the carbohydrate moiety on t-PA has not been determined, it is known, in general, that glycosylation can cause certain differences of which the following are of biological interest: antigenicity, stability, solubility and tertiary structure. The carbohydrate side-chains also can affect the protein's half-life and target it to receptors on the appropriate cells. See, for example, Delente, *Trends in Biotech.* 3 (9), 218 (1985), and Van Brunt, *Bio/Technology* 4, 835–839 (1986). The functional properties of carbohydrate-depleted t-PA are further discussed by Little, et al., *Biochemistry* 23, 6191–6195 (1984), and by Opdenakker et al., "EMBO workshop on Plasminogen Activators," Amalfi, Italy, Oct. 14–18, 1985. The latter scientists report that enzymatic cleavage of carbohydrate side-chains from the melanoma (Bowes) derived t-PA by treatment with α-mannosidase causes an increase in the biologic activity of the modified t-PA.

Cultured normal human cells also have been used as a source of t-PA as can be seen from U.S. Pat. Nos. 4,335,215, 4,505,893, 4,537,860, and 4,550,080. Various cell sources mentioned in said patents are primary embryonic (or fetal) kidney, lung, foreskin, skin and small intestines (Flow Laboratories) or the AG1523 cell line. Brouty-Boye et al., *Bio/Technology* 2 (12), 1058–1062 (1984), further disclose the use of normal human embryonic lung cells for the production of t-PA. Rijken and Collen, *J. Biol. Chem.* 256(13), 7035–7041 (1981), and Pohl et al., *FEBS Lett.* 168(1), 29–32 (1984), disclose the use of human uterine tissue as a t-PA source material. European Patent Application 236,289, published Sept. 9, 1987, describes a uniquely glycosylated t-PA derived from normal human colon fibroblast cells.

Production of glycosylated t-PA in non-human mammalian cells also is known. Thus, Kaufman et al., *Mol. Cell. Biol.* 5, 1750–1759 (1985), and European Patent Application 117,059, published Aug. 29, 1984, describe the use of Chinese hamster ovary cells and Browne et al., *Gene* 33, 279–284 (1985), describe the use of mouse L cells for such production. Kaufman et al., state that the Chinese hamster ovary t-PA is glycosylated in a similar but not identical manner as native t-PA. Glycosylated forms of t-PA obtained by recombinant DNA are further described by Zamarron et al., *J. Biol. Cham.* 259 (4), 2080–2083 (1984), and Collen et al., *J. Pharmacol. Expertl. Therap.* 231 (1), 146–152 (1984).

Production of glycosylated t-PA by recombinant DNA yeast cells also has been reported. Thus, European Patent Application 143,081, published May 29, 1985, describes a recombinant yeast plasmid vector which encodes human t-PA from Hela cells. European Patent Application 174,835, published Mar. 19, 1986, describes a t-PA with selected glycosylation expressed in yeast in which the cDNA encoding for the t-PA is derived from Bowes melanoma. European Patent Application 178,105, published Apr. 16, 1986, discloses a glycosylated uterine t-PA expressed in yeast cells or mouse C-127 cells. In the latter case, a bovine papilloma virus is used as the vector.

Notwithstanding the great variety of sources for obtaining t-PA, one of the problems that exists with the normal t-PA molecule is its relatively short half-life. Intravenously administered t-PA disappears rapidly from the circulation into the liver where it is degraded. The half-life of this clearance is approximately 2 minutes in rabbits [Korninger et al., *Thromb. Haemostas.* 46, 658–661 (1981)]. Recent clinical studies have suggested that the half-life in humans may be slightly longer, on the order of 3-4 minutes [Nilson et al., *Scand. J. Haematol.* 33, 49–53 (1984)]. Since thrombolysis in vivo takes, at best, several hours to achieve, these findings indicate that the successful application of t-PA for thrombolysis in man will require its continuous infusion. Development of a t-PA with a longer half-life would allow for shorter periods of administration or a smaller dose.

Recently, so-called second generation type t-PAs have been prepared by recombinant DNA technology and various protein engineering schemes in attempting to improve the t-PA molecule. It is known that the normal t-PA molecule has five functional domains or regions: A fibronectin-like finger domain (F); an epidermal grown factor region (GF); two kringle regions (K1 and K2); and a serine protease region (SP). In the 527 amino acid sequence of the normal t-PA molecule described by Pennica et al., *Nature* 301, 214–221 (1983), the finger region comprises residues 1–43; the growth factor region comprises residues 44–91; kringle refers to a characteristic triple disulfide structure of which t-PA has two such regions, K1—residues 92–173, and K2—residues 180–261; and the serine protease comprises residues 262–527. The SP catalytic site is formed from the His-322, Asp-371 and Ser-478 residues. Various deletions of one or more of these regions together with elimination of one or more of the glycosylation sites such as by site-directed mutagenesis have been described heretofore. See, for example, Kagitani et al., *FEBS Lett* 189(1), 145–149 (1985); Zonneveld et al., *Proc. Natl. Acad. Sci. USA* 83, 4670–4674 (1986); Verheijen et al., *The EMBO J.* 5 (13), 3525–3530 (1986); Ehrlich et al., *Fibrinolysis* 1, 75–81 (1987); Klausner, *Bio/Technology* 4, 706–710 (1986) and 5, 869–870 (1987); and various abstracts in *Thromb. Haemostasis.* 58, 1–676 (1987). European Patent Applications 234,051, published Sept. 2, 1987, and 242,836, published Oct. 28, 1987, and PCT International Application WO 87/03906, published July 2, 1987, disclose a variety of t-PA mutants having alterations in the arrangement or order of one or more of the functional domains.

Specific examples of t-PA having various other site-directed mutagenesis are as follows:

In European Patent Application 178,105, published Apr. 16, 1986, a modified t-PA is described in which one or more of the glycosylation sites have been eliminated by site-directed mutagenesis of Asn to Gln at the glycosylation sites in the kringle and serine protease regions. The amino acid residues Asn-120, -187 and -451 in the described uterine t-PA are equivalent to residues Asn-117, -184 and -448, respectively, in the Bowes melanoma t-PA. U.K. Patent Application G.B. 2,173,804, published Oct. 22, 1986, describes mutagenesis in the region of residues 270 to 279 to prevent conversion to the two-chain form of t-PA, especially mutagenesis of Arg-275 and Ile-276, e.g. Arg-275→Gly or Glu. In PCT International Application WO 86/01538, published March 13, 1986, the mutant Lys-277→Ile is described. A variety of sitemutagens are also described in European Patent Application 227,462, published July 1, 1987, including mutagenesis at the above glycosylation sites and at the cleavage sites in the region 272–280, especially in the sequence Phe(274)-Arg(275)-Ile(276)-Lys(277).

In copending application Ser. No. 07/149,793, filed Jan. 29, 1988, a modified t-PA is disclosed which has a single site mutation of Arg for Cys at residue 73. This modified t-PA, represented as t-PA[Cys(73)→Arg], was also designated t-PA variant MB1023. The disclosure of said copending application is incorporated herein by reference.

BRIEF DESCRIPTION OF THE INVENTION

In accordance with the present invention a novel modified t-PA has been developed with a substantially improved in vivo half-life. This modified t-PA contains mutations at two sites remote from each other, one in the growth factor (GF) region and the other in the serine protease (SP) region. For convenience, the modified t-PA of this invention can be represented as t-PA[Cys(73)→Arg, Lys(277)-Asp]. In these mutations, a suggested disulfide bond at residue 73 is removed and a highly charged amino acid is substituted; whereas, at residue 277 a basic amino acid is replaced with an acidic amino acid.

In a preferred embodiment, the modified t-PA of this invention was prepared from a chemically synthesized gene coding for t-PA with point mutations of Arg for Cys at residue 73 and Asp for Lys at residue 227. In this embodiment designated herein as t-PA variant MB1083, the mature protein has a 527 amino acid structure in which residue 73 is arginine instead of the cysteine and residue 277 is aspartic acid instead of the lysine that are present in native t-PA. This variant can be prepared by using an oligonucleotide sequence in the construction of the synthetic gene which codes for Arg instead of Cys and Asp instead of Lys at the appropriate positions.

The gene coding for the modified t-PA of this invention can be cloned into and expressed in prokaryotic and eukaryotic hosts. For example, active modified t-PA protein can be expressed in a prokaryotic host such as *E. coli* or a eukaryotic host such as Chinese hamster ovary (CHO) cells or C-127 mouse cells by operably inserting the modified t-PA coding sequence in replicable expression vectors or plasmids. For example, it can be inserted into a suitable plasmid such as pML for production in *E. coli* and the bovine papilloma virus (BPV) vector for production in mouse cells or a shuttle vector which can replicate in both prokaryotic and eukaryotic cells. In a preferred embodiment, the gene coding for the t-PA sequence t-PA[Cys(73)→Arg, Lys(277)→Asp] was cloned into and expressed from C-127 mouse cells. The excreted protein was extracted from the cell media by concentration and then purified on an affinity chromatography column.

The gene coding for the modified t-PA of this invention is conveniently made by first constructing the gene for t-PA variant MB1023, namely t-PA [Cys(73)-Arg], as in copending application Ser. No. 07/149,793, and then making another single point mutation of Asp for Leu at residue 277 of said gene.

A cloning vector containing the nucleotide sequence for the t-PA variant MB1023 is plasmid pMON1401. This plasmid carried in a mouse C-127 host cell is on deposit with the American Type Culture Collection, Rockville, Md., under accession number ATCC CRL 9614. This cloning vector thus is a suitable starting material for preparation of the modified t-PA of the present invention.

The modified t-PA of this invention has a substantially longer half-life (t½) than native t-PA as can be demonstrated by injecting radiolabelled t-PA protein into rats. When measured in a plasminogen dependent rate assay or in an in vitro clot lysis assay, the modified t-PA is less active than the native t-PA.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

FIG. 1 shows the construction of a chemically synthesized gene coding for t-PA assembled from individual oligonucleotides (positioned between the < > symbols) with nucleotide sequences and restriction enzyme sites as shown. Nucleotides are numbered on the right-hand side. The 1609 bp DNA of FIG. 1 is split into Panels A, B and C of FIG. 1.

FIG. 2 shows the nucleotide sequence of a synthetic gene fragment which includes the signal sequence of native t-PA. The 36 amino acids coded by the signal sequence beginning with methionine followed by the first 5 amino acids of the mature protein beginning with serine are shown above the nucleotide sequence.

FIG. 5 shows the nucleotide sequence of the t-PA variant MB1023 spread over 4 panels A, B, C and D. The nucleotides, which include some upstream and downstream processing, are numbered 1 to 1721 on the right-hand side. The corresponding amino acid sequence of the t-PA protein is shown below the nucleotide sequence in the rows labelled "a:" The signal sequence (as in FIG. 2) begins with the methionine at position −35 while the mature protein of 527 amino acids begins with the serine at position +1. An arginine is shown to replace the cysteine at position +73 of native t-PA.

Figure 6:
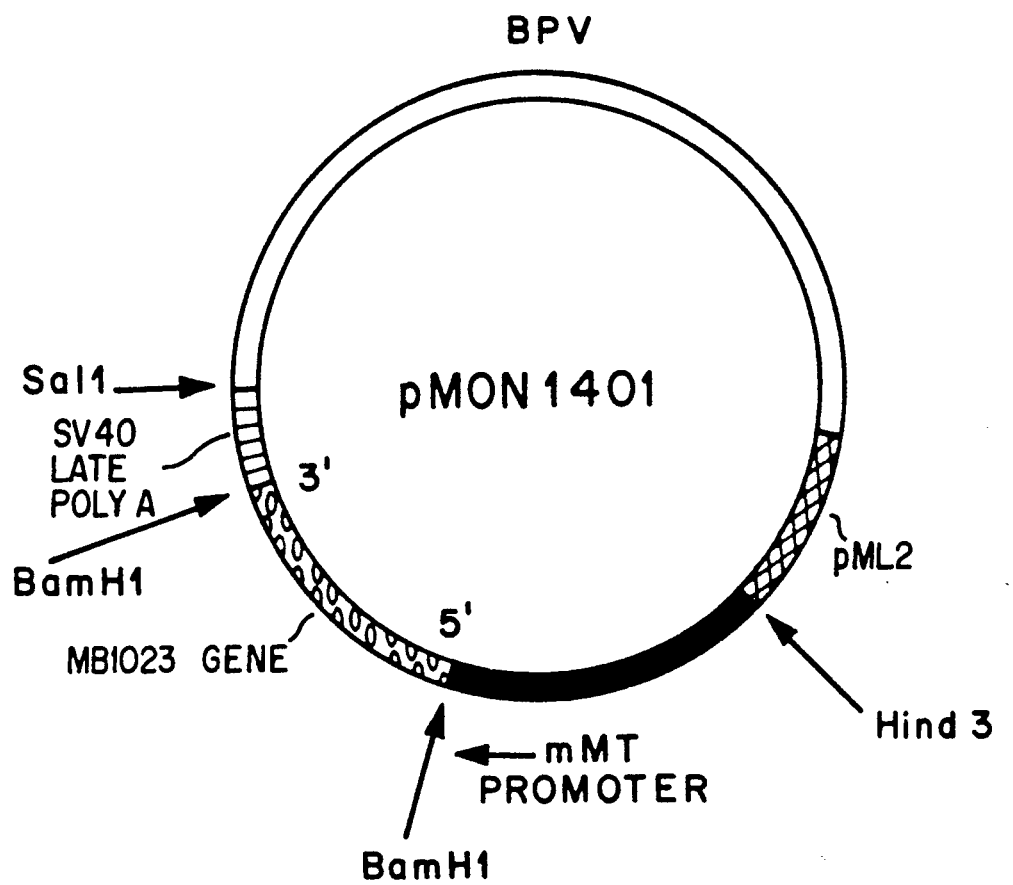

FIG. 6 shows the map of plasmid pMON1401 which is an expression vector for the expression of t-PA variant MB1023 in mouse C-127 cells. In this vector, BPV is the complete bovine papilloma virus genome, SV40 is the late poly(A) addition site of the SV40 virus, mMT is the mouse metallothionien I promoter and pML2 is a derivative of the E. coli plasmid pBR322 with an animal viral insert.

Figure 7:
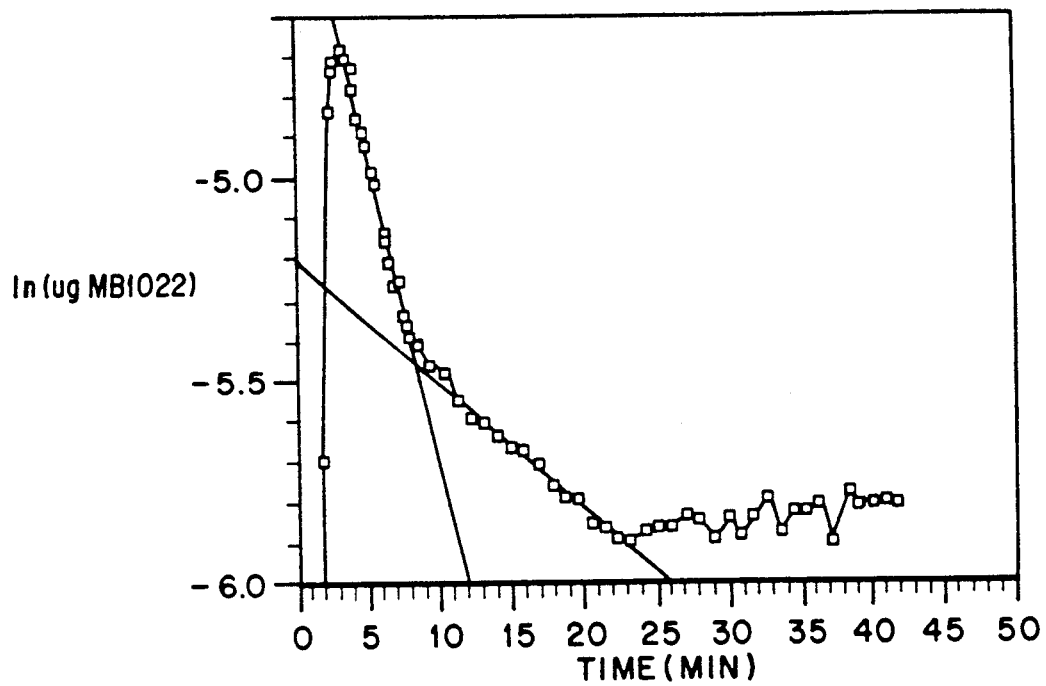

FIG. 7 is a graphical representation which shows the in vivo clearance of Bowes melanoma t-PA (MB1022) in the rat following bolus injection. The half-life (t½) was calculated by linear regression of ln [μg t-PA] vs. time (minutes).

Figure 8:
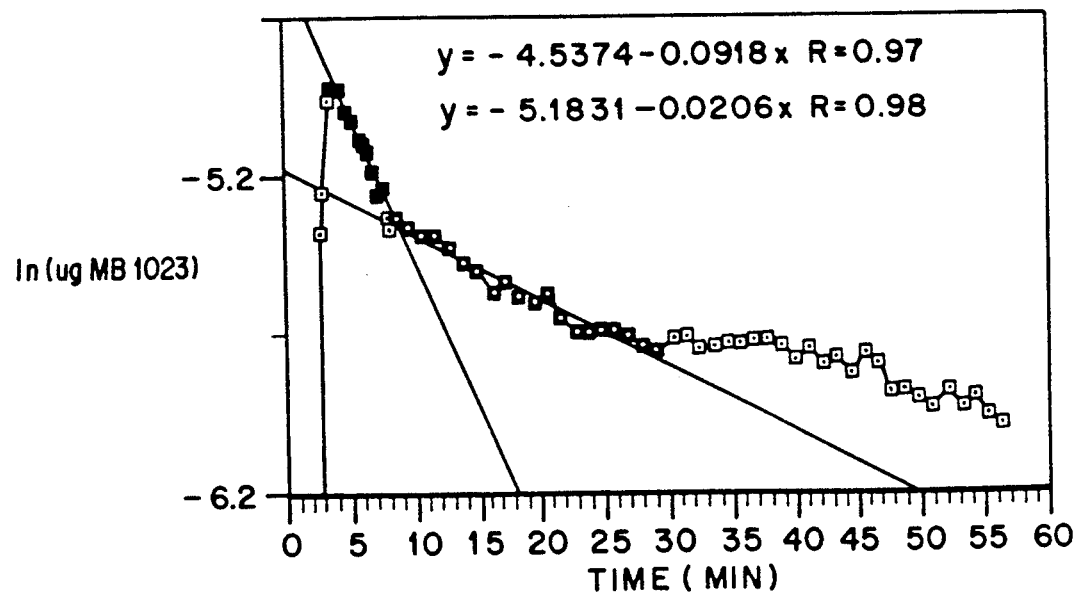

FIG. 8 is a graphical representation which shows the in vivo clearance of t-PA variant MB1023 in the rat following bolus injection. The t½ was calculated as in FIG. 7.

FIG. 9 shows the nucleotide sequence of the t-PA variant MB1083, spread over 4 Panels, A, B, C and D.

The nucleotides, which include some 5' and 3' nontranslated sequences are numbered 1 to 1721 on the right-hand side. The corresponding amino acid sequence of the t-PA variant protein is shown below the nucleotide sequence. The signal sequence and the pro-t-PA sequence begin with the methionine at position −35 while the mature protein of 527 amino acids begins with a serine at position +1. An aspartic acid is shown to replace the lysine at position +277 of MB1023 in FIG. 5.

FIG. 10 shows the oligonucleotide-directed site specific mutagenesis used to create MB1083. The upper line shows the nucleotide sequence and amino acid sequence of MB1023 around position +277. The middle line shows the nucleotide sequence of the mutagenesis primer. The bottom line shows the resulting nucleotide sequence and amino acid sequence of MB1083.

Figure 11:
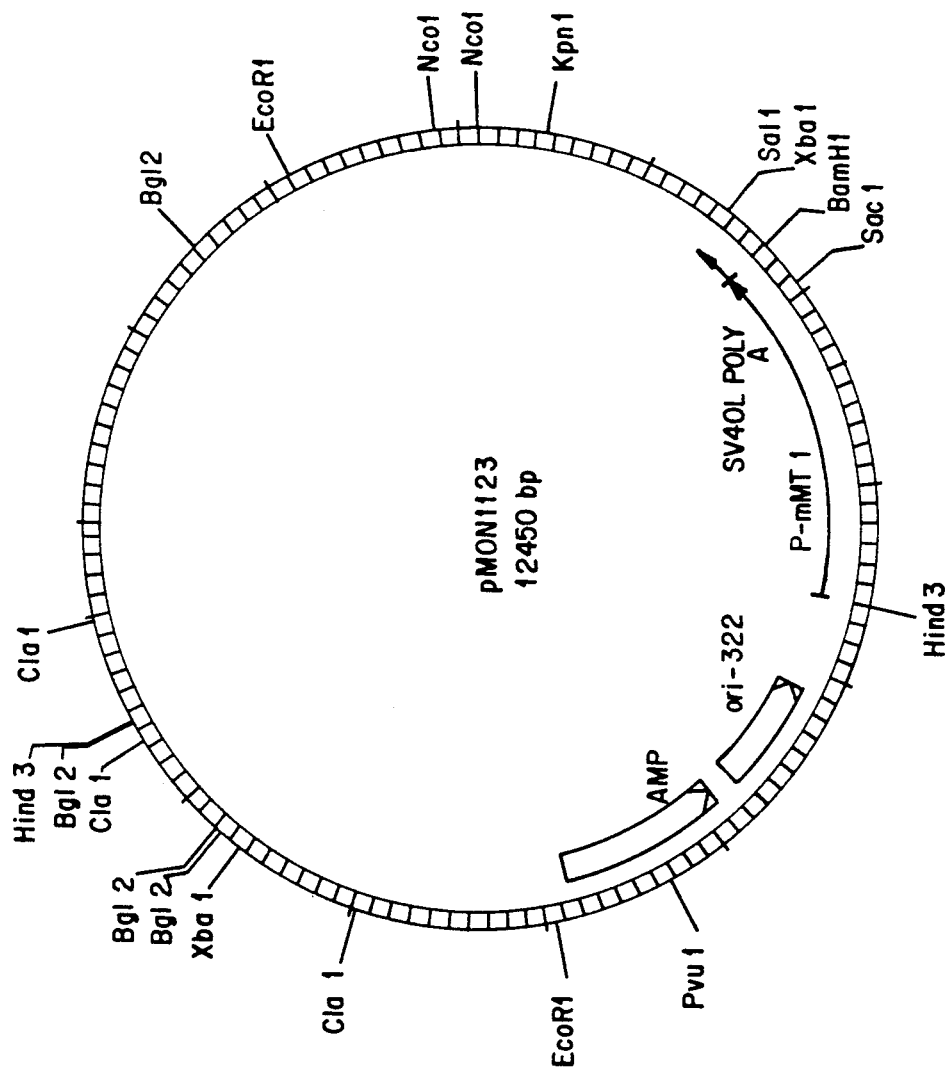

FIG. 11 shows the plasmid pMON1123 which is an expression vector that can be used to express the t-PA variant proteins in C-127 cells. In this vector BPV is the complete bovine papilloma virus genome, SV40 is the late poly(A) addition site of the SV40 virus, mMT is the mouse metallothionein I promoter, and pML2 is a derivative of the E. coli plasmid pBR322.

Figure 3:
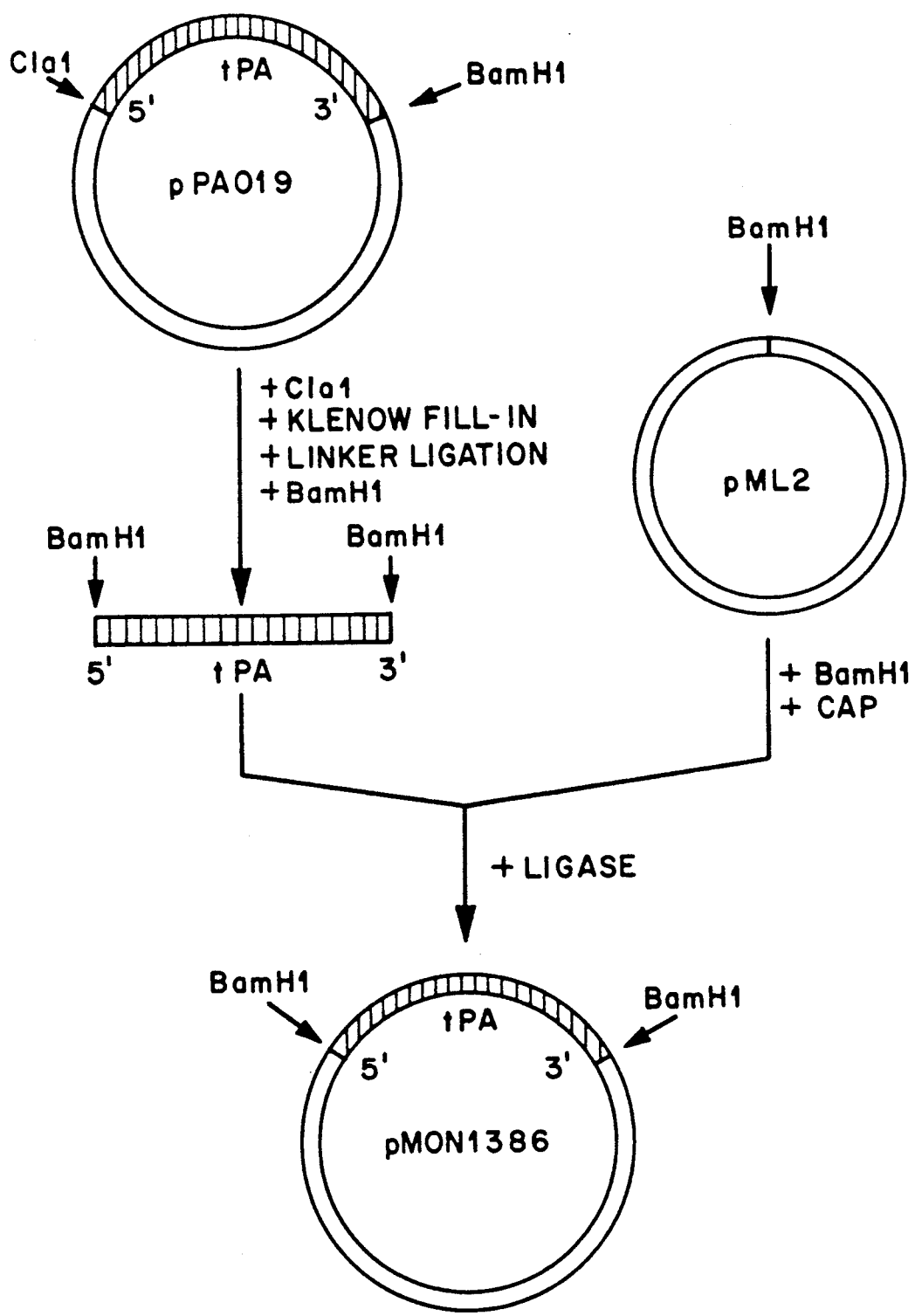
FIG. 3 shows the construction of plasmid pMON1386 of 4326 bp from plasmid pPA019 of 5028 bp and plasmid pML2 of 2600 bp.

The nucleotide sequences of FIGS. 1 and 2 and the construction of pMON1386 of FIG. 3 are also shown in co-pending application Ser. No. 07/107,708, filed Oct. 9, 1987. The nucleotide sequence of FIG. 5 and construction of pMON1399 of FIG. 4 and pMON1401 of FIG. 6 are also shown in co-pending application Ser. No. 07/149,793, filed Jan. 29, 1988.

Standard biochemical nomenclature is used herein in which the nucleotide bases are designated as adenine (A); thymine (T); quanine (G); and cytosine (C). Corresponding nucleotides are, for example, deoxyadenosine-5'-triphosphate (dATP). Amino acids are shown either by three letter or one letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonucleases used herein have the following restriction sequences and (indicated by arrows) cleavage patterns.

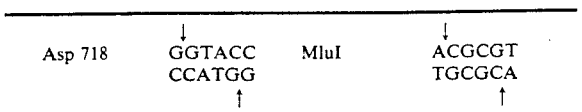

-continued

| | | | |
|---|---|---|---|
| AvaI | ↓<br>CPyCGPuG<br>GPuGCPyC<br>↑ | NcoI | ↓<br>CCATGG<br>GGTACC<br>↑ |
| BamHI | ↓<br>GGATCC<br>CCTAGG<br>↑ | NdeI | ↓<br>CATATG<br>GTATAC<br>↑ |
| BclI | ↓<br>TGATCA<br>ACTAGT<br>↑ | NotI | ↓<br>GCGGCCGC<br>CGCCGGCG<br>↑ |
| BglII | ↓<br>AGATCT<br>TCTAGA<br>↑ | PvuI | ↓<br>CGATCG<br>GCTAGC<br>↑ |
| ClaI | ↓<br>ATCGAT<br>TAGCTA<br>↑ | PvuII | ↓<br>CAGCTG<br>GTCGAC<br>↑ |
| EcoRI | ↓<br>GAATTC<br>CTTAAG<br>↑ | SacI | ↓<br>GAGCTC<br>CTCGAG<br>↑ |
| HincII | ↓<br>GTPyPuAC<br>CAPuPyTG<br>↑ | SalI | ↓<br>GTCGAC<br>CAGCTG<br>↑ |
| HindIII | ↓<br>AAGCTT<br>TTCGAA<br>↑ | StuI | ↓<br>AGGCCT<br>TCCGGA<br>↑ |
| KpnI | ↓<br>GGTACC<br>CCATGG<br>↑ | XbaI | ↓<br>TCTAGA<br>AGATCT<br>↑ |

In order to illustrate specific preferred embodiments of the invention in further detail, the following exemplary laboratory work was carried out. This work includes the construction of a chemically synthesized t-PA gene from selected oligonucleotides and cloning of the gene in a suitable plasmid vector. The cloning and subsequent expression of a 527 amino acid modified t-PA (variant MB1083) having the, protein sequence represented by t-PA[Cys(73)→Arg, Leu(277)→Asp] is thus illustrated in detail.

EXAMPLE 1

CONSTRUCTION OF MB1023

MATERIALS

Enzymes were obtained from New England Biolabs, Boehringer Mannheim Biochemicals or Sigma Chemical Company and used according to the manufacturers printed specifications. Chemicals and components of media were obtained from Sigma Chemical Company and American Scientific Products, respectively. 5'-Dimethoxytritylated N-protected nucleosides were purchased from Cruachem. T4 DNA ligase and T4 polynucleotide kinase were obtained from Amersham International. Controlled pore glass (CPG, 700 Å pore size, 200-400 mesh) was purchased from BDH.

METHODS

Construction of synthetic t-PA gene.

A synthetic t-PA gene was designed as shown in FIG. 1. The codon choice was based on optimum yeast codons, but also includes many restriction endonuclease sites. The gene was divided into oligonucleotides as shown, for the purpose of chemical synthesis.

Preparation of oligonucleotides

Aminopropyl CPG was prepared as described by Chow et al., Nucleic Acids Research 9, 2807-2817 (1981). 5'-Dimethoxytrityl deoxyribonucleoside 3'-0-succinates were synthesized and coupled to aminopropyl CPG following published procedures [Chow et al., Ibid.]. Methyl phosphodichloridite was prepared by the method of Martin and Pizzolato, J. Amer. Chem. Soc. 72, 4584-4586 (1950). 5'-Dimethoxytrityl-deoxyribonucleoside-3'-0-(N,N-diisopropylamino)-methyl phosphoramidites were prepared by a modification of the method of McBride and Caruthers, Tetrahedron Letters 24, 245-248 (1983). Products were precipitated from pentane at −20° C. and used without further purification. Phosphoramidites were stored at room temperature in a dry atmosphere. Oligonucleotides were prepared using an automated synthesizer. Syntheses were carried out in glass columns (bed volume: 6.5 mm I.D.×50 mm, Omnifit) containing 50 mg of derivatized CPG (25 μmole nucleotide/g). After each addition the yield was estimated by spectrophotometric assay of the acid-cleaved dimethoxytrityl cation. At the end of the synthesis the 5'-dimethoxytrityl group was removed by treatment with 3% dichloroacetic acid in dichloromethane. Other protecting groups were removed by treatment with thiophenol-dioxane-triethylamine (1:2:1) for 60 minutes at room temperature, followed by treatment with concentrated ammonia in a sealed vial at 70° C. for 4 hours.

Purification of oligonucleotides

Deprotected oligonucleotides were precipitated from concentrated ammonia by the addition of 0.1 volume of 3M sodium acetate (pH 5.2) and 2.5 volumes of ethanol. After 10 minutes at −70° C., the DNA was recovered by centrifugation. The pellet was washed with 80% ethanol, dried and redissolved in H$_2$O (0.5 ml). An aliquot (20 A$_{260}$ units) was lyophilized and redissolved in formamide (25 μl) containing 0.01% bromophenol blue. The sample was heated for 2 minutes at 90° C. and then analyzed on a 15% denaturing gel (1.6 mm thick). After electrophoresis for 16 hours at 350V, products were visualized by UV shadowing. Oligonucleotides were eluted from the gel slices by soaking overnight in 0.5 M ammonium acetate, 0.01 M magnesium acetate, 0.1% sodium dodecylsulfate (SDS) (500 μl). The solution was through 0.22 μm filters (Millipore) and the DNA recovered by ethanol precipitation. An aliquot of the purified oligonucleotide was analyzed on a denaturing gel after 5'-labelling with polynucleotide kinase and $^{32}$P-ATP.

Assembly of synthetic duplexes

With the exception of the two 5'-terminal oligonucleotides, aliquots of oligonucleotides (100-500 pmoles) were lyophilized and then phosphorylated in a mixture (20 μl) containing 0.1 mM $^{32}$P-ATP (5 μCi/mMole), 50 mM Tris-HCl, pH 7.6, 20 mM dithiothreitol (DTT), 0.1 mM spermidine and 2 units of T4 polynucleotide kinase.

After 60 minutes at 37° C. phosphorylated oligonucleotides were isolated by electrophoresis on 15% denaturing gels. Oligonucleotides were eluted from gel slices as described above. Recovery was determined by Cerenkov counting of aliquots. Phosphorylated oligonucleotides (50 pmoles) were annealed in groups of 5. The oligonucleotides were combined and lyophilized, dissolved in H$_2$O (15 μl), heated to 90° C. for 5 minutes and then slowly cooled to 20° C. Then 10×ligase buffer, 200 mM DTT and 10 mM ATP were added to give a final concentration of 50 mM Tris-HCl, pH 7.4, 10 mM MgCl$_2$, 20 mM DTT, 0.5 mM ATP. T4 DNA ligase (0.5 μl) was added. After 60 minutes at 20° C. the products were ethanol precipitated and analyzed on 10% native gels. Products were eluted as described above and aliquots (1%) were analyzed on denaturing gels. Synthetic oligonucleotides of defined sequence were used as size markers (93-mer, 72-mer, 57-mer, 49-mer, 41-mer, 35-mer).

Duplexes which contained products of the correct length were annealed at 50° C. and ligated together as described above. Products were isolated and analyzed in a similar manner.

Cloning of synthetic duplexes

All synthetic duplexes were initially cloned into the ClaI and BamHI sites of pAT153 (plasmid pPA019 in FIG. 3). The vector was prepared by digestion with ClaI and BamHI restriction endonucleases. After dephosphorylation with calf intestinal phosphatase (Boehringer), the 3.2 kbp fragment was purified by electrophoresis on a 1% agarose gel and recovered by electroelution.

Synthetic duplexes were phosphorylated before ligation to the vector. In a typical run, a 2:1 molar excess of vector:insert was used. Preparation of competent *E. coli* DH1 cells, transformation of cells and selection of ampicillin resistant colonies was carried out as previously described by Hanahan, *J. Mol. Biol.* 166, 557–580 (1983) and Maniatis et al., *Molecular Cloning, A Laboratory Manual*, Cold Spring Harbor Lab., N.Y., (1982).

Colonies were innoculated into L-broth (7 ml) containing L-ampicillin (100 μg/ml, Sigma) and grown up overnight at 37° C. An aliquot was removed for a glycerol stock and DNA was isolated from the remainder of the culture by the method of Holmes and Quigley, *Anal. Biochem.* 114, 193–197 (1981). Colonies containing the insert were identified by restriction enzyme analysis and colony hybridization, using oligonucleotides present in the synthetic gene.

Plasmid DNA for sequence analysis was obtained from larger cultures (500 ml) grown in the presence of chloramphenicol. DNA was isolated by a modification of the method of Clewell and Helinski, *J. Bacteriology* 110, 1135–1146 (1972), and purified on CsCl gradients. The sequence of the synthetic inserts was confirmed by the Maxam-Gilbert method, *Methods in Enzymology* 65, 499–560 (1980).

Figure 4:
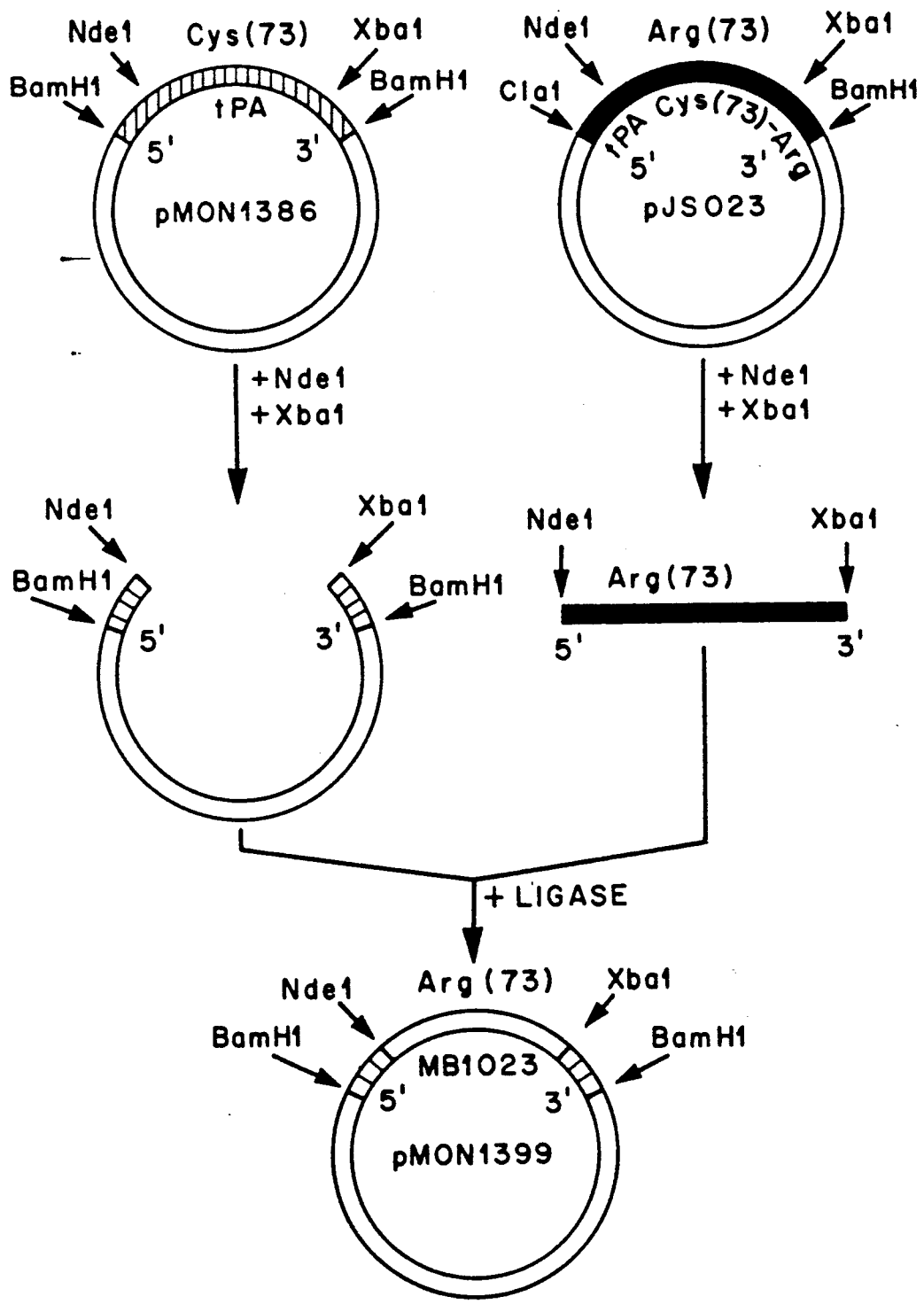
FIG. 4 shows the construction of plasmid pMON1399 from a large vector fragment cut from pMON1386 of FIG. 3 at its unique NdeI and XbaI sites and a 1300 bp fragment of the plasmid pJS023 containing a portion of the t-PA coding for Cys(73)→Arg.

Oligonucleotide PA95 (shown in FIG. 1 as the ninth oligonucleotide in the sequence—residues 217–244) was designed to have the sequence 5'TCTGACTTCGTCTGTCAATGTCCAGAAG 3'. Due to the side reactions that occur during the chemical synthesis the oligonucleotide PA95 was contaminated with the sequence 5'TCTGACTTCGTCCGTCAATGTCCAGAAG 3'. That is, the nucleotide 13 in the 28-mer was C instead of T. This resulted in the isolation and sequence analysis of a colony containing the mutation Cys(73)→Arg t-PA. The pAT153 derived plasmid containing this variant gene is designated pJS023 (FIG. 4). The variant protein derived from this gene is referred to as MB1023. This mutation can also be produced intentionally by substituting the appropriate oligonucleotides coding for arginine at the normal gene position corresponding to Cys(73).

A synthetic gene fragment coding for the natural signal sequence of t-PA (FIG. 2) was cloned into the ClaI - NdeI sites of the correct t-PA gene by methods described above to give the vector pPA019 (FIG. 3).

CONSTRUCTION OF A GENE CODING FOR MB1023

The gene and protein sequences of MB1023 are shown in FIG. 5. The signal sequence starts at amino acid position −35 (as shown) with the mature protein beginning at +1. An arginine residue is shown to replace the cysteine of native t-PA at position +73. Some upstream and downstream DNA sequence is present.

A) Construction of pMON1386

The 5'-ClaI site of pPA019 was converted to a BamHI site by the use of BamHI linkers as outlined in FIG. 3. Thus, pPA019 was digested with ClaI and the resulting 5'-overhanging ends were converted to blunt ends with Klenow fragment of DNA polymerase. BamHI linkers having the sequence 5'-CCGGATCCGG-3'(Pharmacia P-L Biochemicals) were then ligated onto these ends with T4 DNA ligase. After ligation the DNA was digested with BamHI and the resulting 1710 bp t-PA fragment was isolated using NA-45 DEAE membrane as described in Schleicher and Schuell technical literature 364. The purified fragment was then ligated into the BamHI site of the plasmid pML2. This mixture was used to transform *E. coli* HB101 cells to yield the plasmid pMON1386. Klenow fill-in reaction, ligation and transformation were done as described in Maniatis et. al., *Molecular Cloning, A Lab. Manual*, Cold Spring Harbor Laboratory, N.Y. (1982).

B) Construction of pMON1399

A synthetic t-PA BamHI expression cassette possessing the Cys(73).Arg change was constructed by exchange of NdeI-XbaI fragments between pMON1386 and pJS023 (FIG. 4). pMON1386 was digested at its unique NdeI and XbaI sites and the large vector fragment was isolated. Similarly pJS023 was digested with NdeI and XbaI and the 1300 bp fragment containing a portion of the t-PA coding region with the Cys(73-)→Arg change was isolated. The pJS023 NdeI-XbaI fragment was then ligated into the NdeI-XbaI cut pMON1386 to yield pMON1399. This plasmid contains the MB1023 Cys(73)→Arg t-PA with BamHI sites at the 5' and 3' ends of the synthetic gene.

Expression of MB1023

The t-PA variant MB1023 BamHI fragment was isolated by BamHI digestion of pMON1399. Following purification, this fragment was ligated into the unique BamHI site of the expression vector pMON1123 by reaction with T4 ligase using standard conditions [Maniatis et al. *Molecular Cloning, A Lab. Manual*, Cold Spring Harbor Laboratory, N.Y. (1982)]. The pMON1123 expression vector is based on the bovine papilloma virus/pML2 plasmid pPBV2308 (a gift of Dr. Dean Hamer, National Institutes of Health). pMON1123 was constructed by insertion of DNA fragments encoding the mouse metallothionien 1 promoter and the SV40 Late poly A addition site in such a way that these two fragments are separated by a unique BamHI site. DNA fragments inserted into this BamHI site are therefore expressed using the metallothionien promoter and SV40 Late poly A site regulatory signals. Insertion of the MB1023 BamHI fragment into pMON1123 yielded the plasmid pMON1401 (FIG. 6).

C-127 cells (mouse mammary tumor cells) (ATCC CRL 1616) were grown in high glucose Dulbecco's modified Eagles medium (DMEM) containing 5% heat-inactivated fetal bovine serum, 1X penicillin-streptomycin, and 1X glutamine. Twenty four hours prior to transfection, cells were seeded in 60 mm dishes at $4 \times 10^5$ cells per dish. Cells were cotransfected with a mixture of pMON1401 and pSV2neo [Southern and Berg, *J. Molec. Appl. Genet.* 1, 327–341 (1982)] by the calcium phosphate precipitate method of Wigler et al, *Cell* 16, 777 (1979). Twenty four hours after transfection the 60 mm plates were each split 1:10 into 100 mm dishes containing high glucose DMEM, 5% heat-inactivated fetal bovine serum, 1X penicillin-streptomycin, 1X glutamine, and 50 KIU of aprotinin. This media was also supplemented with 800 $\mu$g/ml of the antiobiotic G418 (genticin) (GIBCO) for selection of neomycin resistant transfectants [Southern and Berg, supra]. After two weeks of selection G418 resistant colonies appeared. These colonies were screened for M1023 production by the use of a fibrin overlay screen performed essentially by the method of Cederholm-Williams et al., in "Treatment of Metastasis: Problems and Prospects," Hellman and Eccles, Eds. (Taylor and Francis, London and Philadelphia) pp. 347–350 (1985). Each plate was overlayed with a 1.2% agarose matrix containing Dulbecco's minimal Eagles medium, 0.1 U/ml bovine thrombin (CalBiochem), 3 mg/ml bovine fibrinogen (CalBiochem), and 0.07/ml human plasminogen (Kabi). Following incubation at 37° C., clearing zones in the fibrin matrix appeared over specific colonies. These colonies were picked and seeded into wells of 24 well plates. Each well was allowed to grow to confluency and then expanded into a T75 flask to establish a stable line. The expression level of these lines was monitored by a t-PA specific ELISA (American Diagnostica).

The cell line having the highest expression levels was expanded into multiple T75 flasks. These cells were used to seed a 6000 cm$^2$ cell factory (Nunc). The cells were allowed to proliferate in the normal growth media until confluent. At this time the cells were washed with phosphate buffered saline containing Ca$^{+2}$ and Mg$^{30\,2}$ and were then fed with serum-free DMEM containing 2X penicillin-streptomycin, 1X glutamine, 50 KIU/ml aprotinin, and 0.3% lactalbumin hydrolysate. Conditioned media was replaced with fresh media every 3 days and used for protein purification.

MB1023 isolation

Purification of MB1023 was achieved by affinity chromatography on an Erythrina inhibitor-Sepharose® 4B column [Heussen et al, *J. Biol. Chem.* 259, 11635–11638 (1984)]. The conditioned medium was concentrated by ultrafiltration on Amicon's YM 30 spiral membrane system. The concentrates were made up to 0.5 M NH$_4$HCO$_3$, 1% Triton X-100 and centrifuged at $26,000 \times$ g for 1 hr. The supernatant was then loaded onto an Erythrina inhibitor-Sepharose 4B column ($6 \times 2.5$ cm). The column was washed with 300 ml of 0.5 M NH$_4$HCO$_3$, 1% Triton X-100 and then with 50 mM NH$_4$HCO$_3$ until detergent free. The bound MB1023 was then eluted with 2.5 M KSCN, 50 mM Na$_3$PO$_4$, pH 7.3. The eluted MB1023 was then dialyzed extensively against 1 M NH$_4$HCO$_3$. The whole purification process was carried out at 4° C.

Amino Acid sequence analysis

Automated Edman degradation chemistry was used to determine the NH$_2$-terminal protein sequence. An Applied Biosystems, Inc., model 470A gas phase sequencer (Foster City, CA) was employed for the degradation [Hunkapiller et al., *Methods Enzymol* 91, 399–413 (1983)]. The respective PTH-aa derivatives were identified by RP-HPLC analysis in an on-line manner employing an Applied Biosystems, Inc., Model 120A PTH Analyzer fitted with a Brownlee 2.1 mm I.D. PTH-C18 column.

Protein determination

The protein concentration of MB1023 was determined by measuring absorbance at 280 nm and assuming that a concentration of 1 mg/ml gives an absorbance of 1.75.

Assays of enzymatic activity

The amidolytic activity of MB1023 was measured using a synthetic substrate, S-2288 (H-D-isoleucyl-L-propyl-L-arginine-p-nitroanilide). The reaction mixture contains 10 $\mu$l of 20 $\mu$g/ml MB1023 in PBS, 5 mg/ml BSA, 2.5 mg/ml bovine gamma globulin, 10 $\mu$l of 0.01 M S-2288, and 230 $\mu$l of 0.1 M Tris-HCl, pH 8.7, 0.5% Triton X-100. Amidolysis was followed by measuring the absorbance change with time at 405 nm.

The plasminogen activator activity of MB1023 was determined by a parabolic rate assay system as follows: Standard t-PA (0–15 I.U/ml) or MB1023 were prepared in a PBS solution containing 5 mg/ml BSA and 2.5 mg/ml bovine gamma globulin (PBB). Twenty $\mu$l of the t-PAs were mixed with 20 $\mu$l of human fibrinogen (2 mg/ml in 0.15 M NaCl) in microfuge tubes and placed on ice. To each tube was added 60 $\mu$l of a reaction cocktail which consisted of 20 $\mu$l of P-buffer (0.25 M Tris-HCl, pH 7.35, 0.5 M NaCl, 25 mM EDTA), 5 $\mu$l of 3 mg/ml plasminogen, 5 $\mu$l of S-2251 (H-D-Val-Leu-Lys-p-nitroanilide), 5 $\mu$l of 20 U/ml human thrombin, 1 mg/ml BSA, and 25 $\mu$l H$_2$O. These were kept on ice until the cocktail was added to all the tubes. The tubes were then transferred to a water bath and incubated at 37° C. for 1.5 hr. To stop the reaction, 0.2 ml of 10% acetic acid was added to each tube. After a brief vortexing and centrifugation, the supernatants were transferred to a 96-well plate for absorbance measurement at 410 nm using a control (without added t-PA) as reference. The activity of the t-PA MB1023 was determined by comparing the A$_{410}$ with that of standard t-PA.

In this assay, it was found that a batch of melanoma single-chain t-PA obtained from American Diagnostica (lot 47-10) has a specific activity of 769±21 I.U./ug using WHO t-PA standards as reference. Because of limited supply of WHO standard, American Diagnostica's t-PA (lot 47-01) was subsequently used as the standard.

Plasma clot lysis assay

The standard t-PA and MB1023 induced plasma clot lysis assay was performed essentially as described by Wun and Capuano, *J. Biol. Chem.* 260, 5061–5066

(1985). In brief, plasma was supplemented with $^{125}$I-fibrinogen and 0.02% NaN$_3$ and divided into 95 μl aliquots in microfuge tubes. Five μl of a solution containing 100 NIH units/ml of thrombin and various amounts of standard t-PA or MB1023 were added to each microfuge tube. The clots were incubated at 37° C. At various time intervals a tube was taken, vortexed, and centrifuged to separate the serum. The percent of clot lysis was calculated based on the amount of $^{125}$I- fibrin degradation products released into serum.

Preparation of $^{125}$I-t-PAs

Iodination of t-PAs was carried out by the Iodo-Bead (Pierce) method [Markwell, *Anal. Biochem.* 125, 427–432(1982)]. Ninety μl of MB1023 (1.0 mg/ml) was mixed with an Iodo-Bead and 5 μl of Na$^{125}$I (0.5 mCi) and incubated at room temperature for 8 min. Then, the mixture was chromatographed on a 5 ml Sephadex G25 (fine) column pre-equilibrated in 1 M NH$_4$HCO$_3$. Fractions of 0.2 ml were collected and the radioactive protein peak was pooled and dialyzed against 1M NH$_4$HCO$_3$.

In vivo clearance of t-PAs in rat

Wistar rats (~300 g) were anesthetized by intraperitoneal injection of sodium pentobarbital. The rat was then cannulated at the right jugular vein and carotid artery using polyethylene tubing (I.D. 0.58 mm; O.D. 0.97 mm). The cannula of the carotid artery was connected to silicon tubing (I.D. 0.63 mm; O.D. 1.2 mm) which feeded through a larger tubing (I.D. 1.3 mm; O.D. 3.3 mm) of a microperpex peristaltic pump (LKB). Blood was collected into a fraction collector. A heparin solution was injected through the jugular vein such that the concentration in circulation was approximately 2 units/ml, assuming that the blood volume is 7 ml per 100 g body weight. After 5 min., 15 μg of $^{125}$I-t-PA was injected through the jugular vein and the blood was pumped into fraction collector at a speed of 30 μl/fraction/20 sec initially, and at 30 μl/fraction/60 sec after 25 fractions were collected. The time course of the clearance of MB1023 is followed by counting the radioactivity in each fraction of blood collected. Half-life of MB1023 was calculated by linear regression of ln (t-PA) vs. time. The half-life (t½) was calculated from the formula $$t_{\frac{1}{2}} = \frac{\ln 0.5}{S},$$

S being the slope of the regression line.

Rabbit jugular vein thrombolysis assay

Clot lysis in vivo was studied using a rabbit jugular vein thrombolysis model as described by Collen et al., *J. Clin. Invest.* 71, 368–376 (1983).

ASSAY RESULTS

Isolation of MB1023

The C-127 cells transfected with MB1023 gene were grown in culture and the serum-free conditioned medium was collected for purification of MB1023 using Erythrina inhibitor Sepharose 4B as described above. From 8 L of medium, 33 mg of MB1023 was isolated.

Enzymatic activity of MB1023

The enzymatic properties of the MB1023 were assessed by a number of assays and compared to melanoma t-PA (MB1022). In the amidolytic assay system described above, both MB1022 and MB1023 t-PAs gave a rate of absorbance change of 0.0148 units/min.

In the parabolic rate assay, consisting of fibrin-plasminogen-S2251 and t-PAs, the MB1022 possesses a specific activity of 769 I.U./μg. In comparison, the MB1023 has a specific activity of 53 I.U./μg.

In the plasma clot lysis assay, the concentration of MB1023 required to lyse 50% of the clot in 4 hr at 37° C. is 106 ng/ml, in comparison to that for MB1022 t-PA which requires 17 ng/ml. These in vitro data suggest that MB1023 has 6–14 fold decrease in fibrin-specific activity compared to MB1022 t-PA.

Clearance of MB1023 in the rat

As shown in FIG. 7, the clearance of melanoma t-PA MB1022 in the rat after bolus injection follows biphasic kinetics with an initial rapid decline (t½ alpha=4.4±0.1 min, n=3) followed by a slower decline (t½ beta=19±3 min, n=2). In comparison, MB1023 shows an t½ alpha=7.9±0.4 min and t½ beta=28±7 min. (n=2). (FIG. 8).

Thrombolysis in rabbit

Thrombolysis was performed using a rabbit jugular vein model either by infusion of t-PAs over a 4 hour period and measuring the lysis at 4.5 hr or by a bolus injection over 10 min and measuring the lysis at 2 hr. In the infusion study, lysis was 88±1% (n=2) at 1 mg/kg, 67±9% (n=5) at 0.5 mg/kg, and 41±16% (n=2) at a 0.25 mg/kg for control C127 t-PA; and 76±18% (n=4) at 0.5 mg/kg for MB1023. In the 10 min bolus injection study, lysis after 2 hr was 57% (n=1) for control C127 t-PA and 86±0% (n=2) for MB1023, both at 0.5 mg/kg dose. These studies indicate that MB1023 is more thrombolytic than the control C127 t-PA.

EXAMPLE 2

CONSTRUCTION OF MB1083

The gene for MB1023 as constructed in Example 1, above, was used as a starting material for the construction of MB1083. Thus, t-PA variant MB1083 was constructed by changing the Lys residue at position 277 to Asp. The DNA sequence and encoded protein sequence of MB1083 is shown in FIG. 9. Oligonucleotide-directed site specific mutagenesis of the MB1023 gene to create the Lys(277)→Asp change was carried out by the method of Taylor et al., *Nuc. Acids Res.* 13, 8749-8764 (1985) and *Nuc. Acids. Res.* 13, 8765-8785 (1985). The oligonucleotide primer employed for the mutagenesis is synthesized to provide the structure:

5'AATTCAGAATTGACGGTGGTTTAA 3'

As shown in FIG. 10, this primer converts Lys(277) to Asp. The mutagenesis of the MB1023 gene in M13mp18 cloning vector was carried out using the Amersham (Arlington Heights, Ill.) Oligonucleotide-directed In Vitro Mutagenesis System according to the published instructions of the manufacturer. Following mutagenesis, positive mutant genes were identified by DNA sequence analysis using the Sequenase DNA Sequencing System of United States Biochemical Composition (Cleveland, Ohio) [Tabor and Richardson, *Proc. Natl. Acad. Sci. USA* 84, 4767-4771 (1987)].

EXPRESSION OF MB1083

The gene coding the t-PA variant MB1083 is isolated from the M13mp18 cloning vector by digestion with BamHI and purification of the DNA fragments by electrophoresis on agarose gels. This purified t-PA variant MB1083 BamHI fragment is ligated into the expression vector pMON1123 (FIG. 11) to form pMON4590 which is then used for cotransfection with pSV2neo into C-127 cells and expression of t-PA variant MB1083 protein under conditions and procedures similar to that used for production of t-PA variant MB1023 protein in Example 1.

The modified t-PA of the invention can be used for the treatment of thrombolytic conditions by suitable administration to a patient in need of such treatment. The amount of the t-PA which would normally be administered is primarily dependent upon the physical characteristics of the recipient and the severity of the thrombolytic condition. The amount to be administered must be an effective amount, that is, an amount which is medically beneficial but does not present toxic effects which overweigh the advantages which accompany its use. The preferable route of administration is parenteral, especially intravenous. Intravenous administration of the t-PA in solution with normal physiologic saline is illustrative. Other suitable formulations of the active t-PA in pharmaceutically acceptable diluents or carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention and it is intended that all such other examples be included within the scope of the appended claims.

What is claimed is:

1. A modified human tissue plasminogen activator having an improved in vivo half-life compared to native human tissue plasminogen activator, the modification consisting of the substitution of arginine for cysteine at the position corresponding to position 73 and the substitution of aspartic acid for lysine at the position corresponding to position 277 in the 527 amino acid sequence of native human t-PA.

2. A modified human tissue plasminogen activator having the amino acid sequence shown in FIGS. 9A, 9B, 9C and 9D.

3. An isolated, purified DNA sequence encoding the modified human tissue plasminogen activator of claim 1.

4. An isolated, purified DNA sequence encoding the modified human tissue plasminogen activator of claim 2.

5. An isolated, purified human tissue plasminogen activator gene having the nucleotide sequence shown in FIGS. 9A, 9B, 9C and 9D.

6. An expression vector comprising the DNA sequence of claim 3.

7. An expression vector comprising the DNA sequence of claim 4.

8. An expression vector comprising the human tissue plasminogen activator gene of claim 5.

9. Plasmid pMON1123 ligated with the gene of claim 5 between the mouse metallothionien I promoter and the late poly addition site of the SV40 virus.

10. Mouse C-127 cells transformed with the plasmid of claim 9.

11. A process for preparing the modified human tissue plasminogen activator of claim 1 which comprises culturing under conditions sufficient to produce said tissue plasminogen activator a suitable eukaryotic host cell which has been transformed with a replicable expression vector comprising the DNA coding for said human tissue plasminogen activator.

12. A pharmaceutical composition comprising the modified human tissue plasminogen activator of claim 1 and a pharmaceutically acceptable diluent or carrier.

* * * * *